United States Patent [19]
Eyal et al.

[11] Patent Number: 6,037,151
[45] Date of Patent: Mar. 14, 2000

[54] PROCESS FOR THE PREPARATION OF LONG-CHAIN ALKYL GLYCOSIDES

[75] Inventors: Aharon Meir Eyal; Sofia Kotlyar; Francoise Appelbaum; Shlomo Magdassi; Sergei Braun, all of Jerusalem, Israel

[73] Assignee: Yissum Research Development Company of the Hebrew, Jerusalem, Israel

[21] Appl. No.: 08/954,626

[22] Filed: Oct. 20, 1997

Related U.S. Application Data

[63] Continuation of application No. 08/809,330, filed as application No. PCT/GB95/02373, Oct. 6, 1995, Pat. No. 5,845,507.

[30] Foreign Application Priority Data

Oct. 9, 1994 [IL] Israel ......................................... 111208

[51] Int. Cl.$^7$ ............................. C12P 19/44; C07H 15/00
[52] U.S. Cl. .............................. 435/74; 435/72; 536/18.5; 536/18.6
[58] Field of Search .................. 536/18.6, 18.5; 435/72, 74

[56] References Cited

U.S. PATENT DOCUMENTS 5,773,256  6/1998  Pelenc ........................................ 435/74

FOREIGN PATENT DOCUMENTS 2 680 373  2/1993  France .
58-43792   3/1983  Japan .
3-236788  10/1991  Japan .

OTHER PUBLICATIONS

Chahid et al., *Biotechnology Letters*, vol. 14, No. 4 (Apr. 1992), pp. 281–284.
Shinoyama et al., *Agric. Biol. Chem.*, 52:2375–2377 (1988). Months Not Available.
Shinoyama et al., *Agric. Biol. Chem.*, 55:1679–1681 (1991). Months Not Available.
Vulfson et al., *Biotechnology Letters*, 12:397–402 (Jun. 1990).
Vulfson et al., *Enzyme Microbiol. Technol.*, 12:950–954 (Dec. 1990).
Patent Abstracts of Japan, vol. 7, No. 131 (C–169), Jun. 8, 1983.
Laroute et al., *Biotechnology Letters*, 14:169–174 (Mar. 1992).
Gais et al. *Tetrahedron Letters* 1988, 29(45), 5743–44. Months Not Available.
Nilsson *Carbohydrate Research* 1987, 167, 95–103. Months Not Available.

*Primary Examiner*—Kathleen K. Fonda
*Attorney, Agent, or Firm*—Foley & Lardner

[57] ABSTRACT

The invention provides a process for the preparation of long-chain alkyl glycosides, comprising reacting a glucose-containing reactant and a $C_8$–$C_{18}$ fatty alcohol in the presence of a glucosidase and a reaction promoter effective to promote the formation of the alkyl glycoside when the promoter is present in an amount of less than about 50 wt % of the total reaction mixture.

11 Claims, No Drawings

PROCESS FOR THE PREPARATION OF LONG-CHAIN ALKYL GLYCOSIDES

This application is a continuation of U.S. application Ser. No. 08/809,330, filed May 9, 1997, now U.S. Pat. /no. 5,845,507 which was the National Phase Application of International Application No. PCT/GB95/02373, filed Oct. 6, 1995.

The present invention relates to a process for the preparation of long-chain alkyl glycosides.

More particularly, the present invention relates to an enzymatic process for the preparation of long-chain alkyl glycosides.

As described, e.g., as background in U.S. Pat. No. 5,191,071, which is directed to monoesters of glycosides, surface active compounds constitute an exceedingly important class of industrial organic chemicals finding a wide variety of uses, e.g., as detergents for washing purposes, as emulsifiers in food and feed products, or even as functional ingredients in many personal care products, such as shampoos, moisturizing creams, etc.

Basically, on the molecular level, surfactants are characterised by and owe their properties to the presence of hydrophobic and hydrophilic regions within the individual surfactant molecules. This particular constellation can be established in numerous fashions, e.g., by combining sulphonic acid residue, a quarternised ammonium entity or a glycerol moiety with an alkyl chain, as is the case in the linear alkyl sulfonates, the quarternised alkyl amines, and the monoglycosides, respectively. In the actual design of such surfactant molecules, major consideration is given to the detailed molecular architecture of the compounds, important issues being the precise balance between the hydrophilic and hydrophobic domains of the surfactant molecules and the actual special arrangements of these parts of the molecules. Besides, consideration is obviously given to the possibilities of actually producing the surfactants in high yielding processes and on the basis of raw materials available at reasonable costs. The environmental issues related to the eventual loading of the surfactant into the environment are finally a matter of major concern.

Due to the above considerations, over the years there has been a keen interest in preparing surfactant molecules on the basis of sugars and fatty acids or fatty alcohols, e.g., as sugar esters or ethers. Such conjugates were expected to exhibit surface active properties due to the presence of the hydrophilic sugar regions and the hydrophobic fatty acid or fatty alcohol residues. The balance, and thus the precise properties of the conjugates, might be varied through changes of the nature of the sugar and the fatty acid or fatty alcohol residues; the materials would be produceable from exceedingly cheap raw materials; and the surfactants, being composed of, and degradable into, natural constituents, would not be harmful to the environment.

As described and discussed by D. Balzer in *Tenside Surf. Det.*, Vol. 28, p. 6 (1991), alkyl polyglucosides were described for the first time about 100 years ago. However, it was not until 1934 that their potential as surface active substances was appreciated in a patent to H. Th. Boehme AG of Chemnitz. They then fell into obscurity for a long time, probably because not only were they difficult to manufacture, especially as regards the control of the colour quality, but also because of the many surfactants already in production. It was not until about 10 years ago that this old class of surfactants was unearthed again, against a background of increasing environmental concerns, but also because of the spectre of a raw material, i.e., crude oil, shortage.

Alkyl polyglucosides are non-ionic surfactants prepared on the basis of renewable raw materials, namely, starch and fat, or their derivatives glucose and fatty alcohols. By utilising D-glucose, probably the most common natural organic monomer unit, as a surfactant base, the range of raw materials for surfactants is advantageously expanded. This statement is underlined by the excellent application properties and favourable eco-tox data of the alkyl polyglucosides.

Thus, in recent years, several companies have begun to market-alkyl polyglycoside surfactants.

In the 1980's, it was reported that Horizon Chemical, a newly-formed division of A.E. Staley Manufacturing Co., was commercializing a new generation of alkyl polyglycoside surfactants, superior in quality to surfactants offered, and suitable for use in a wide range of surfactant applications, including household laundry, dishwashing and general purpose cleaners.

The alkyl polyglycosides were described as being non-ionic in nature, but with properties much different from ethoxylated fatty alcohols or alkyl phenols.

As described in said press release, the alkyl polyglycoside surfactants can be used as primary surfactants, or in combination with other surfactants. Synergistic performance has been observed when alkyl polyglycosides are combined with both linear alkylbenzene sulfonate (LAS) and linear alcohol ethoxylate (LAE).

These surfactants are more soluble than other surfactants and are stable under a wide range of conditions. They are milder to the skin than LAS and LAE, and are non-toxic and readily biodegradable. Their foam characteristics in combination with anionic surfactants, combined with their mildness and solubility, allows, for the formulation of a mild, high performance hand dishwashing product with non-ionic grease-cutting ability, but requiring less hydrotrope and no foam booster.

The solubility of the alkyl polyglycoside surfactants in concentrated electrolyte solutions allows the formulation of a stable, concentrated surfactant solution, containing 20–30% of a conventional inorganic builder. In addition, the solubility and solvent properties of these surfactants allow the formulation of a hard surface cleaner which requires no rinsing and less solvent than current products. The solubility, self-hydrotroping and electrolyte compatibility of alkyl polyglycoside surfactants enable slurry concentrations to be increased, thereby allowing processing rates to be raised and cost to be reduced.

The development of copious amounts of stable foam is a primary criteria for a premium dishwashing liquid. Other important factors include mildness and grease emulsification. Alkyl polyglycoside surfactants, unlike ethoxylated fatty alcohols, bring non-ionic grease-cutting strength and mildness to hand dishwashing. These properties make them an ideal surfactant for this end use.

In a press release issued Jan. 5, 1993, it is reported that Henkel Cospha Dusseldorf launched what it describes as a new generation of surfactants, specially developed for the cosmetics industry and sold under the product name Plantaren. Plantaren is an alkyl polyglycoside from renewable raw materials: glucose derived from corn, and fatty alcohols from coconut and palm kernel oils. It is also biodegradable under aerobic and anaerobic conditions. These non-ionic surfactants are said to provide a broad spectrum of possibilities for formulation in the cosmetics sector. Plantaren surfactants are described as being suitable for a variety of personal care applications, such as shampoos, hair conditioners, facial cleansers and bath products, and are found to have very good foaming and cleaning performance, with extraordinary mildness to skin and eyes.

It will thus be realized that alkyl glycosides are now becoming major surfactants of interest and use.

Several patents have issued which propose various processes for the production of alkyl glucosides, e.g., European Patents 0096917 and 0132043 and U.S. Pat. Nos. 3,839,318; 4,393,203; 5,206,357 and 5,212,292. All of said patents, however, are carried out at a temperature range of about 80–150° C. and mostly in a preferred range above 100° C., which presents serious drawbacks in that, at said temperatures, there is both undesirable isomerization and caramelization of sugars, resulting in discoloration and a consequent need for complicated and/or expensive purification steps.

Thus, it will be realized that at the relatively high temperatures and in the presence of an acidic catalyst, many undesirable reactions take place, resulting in difficulties in controlling production in terms of the isomer formed and in the number of glucose groups in the product molecule, forming by-products of lower biodegradability and, what seems to be even more problematic, adding coloring compounds to produce a dark-colored product. Many attempts have been made to reduce the decoloration, e.g., through the gradual addition of the sugar at a rate that limits the amount of unreacted sugar in the reaction mixture to less than 10% by weight [see, e.g., EP 0096917]. Other suggested routes include selecting a better catalyst [U.S. Pat. No. 5,206,357 and EP 0132043] and lowering the acidity and the temperature. Alternatively, processes were proposed for removing the color from the product through treatment with various reducing acids. Thus, e.g., U.S. Pat. No. 4,762,918 teaches a process for reducing the color of a glycoside composition including contacting the glycoside composition under hydrogenation conditions with a hydrogenation catalyst in the presence of hydrogen.

Similarly, U.S. Pat. No. 5,104,981, issued in 1992 and filed in 1989, also states, in column 1, lines 23–26, that "the most serious problem in the production of alkyl glycosides is that various procedures during the production process thereof frequently cause deterioration of the hue of the product." Said patent, after discussing the problems in other prior art patents, teaches that "these materials causing coloration may be readily reduced by contacting the alkyl glycoside reaction product containing these materials with a specific metal/hydrogen complex."

In view of the difficulties encountered in production of these compounds by chemical means and their attractiveness as industrial surfactants, much attention has been devoted during recent years to the possibility of utilising enzymes for synthesis thereof. One major rationale behind this interest is that enzymes are known to exhibit a high degree of regio- and enantioselectivity, which might be exploited for selective etherification of a -hydroxy group in a sugar molecule, and which are used effectively at conditions of mild temperature and mild pH. Two articles describing this approach have been published in 1992. The first is an article by Z. Chahid, et al., entitled, "Effect of Water Activity on Enzymatic Synthesis of Alkyl Glycosides," *Biotechnology Letters,* Vol. 14, No. 4, pp. 281–284 (April 1992). The second is an article by V. Laroute, et al., entitled "Glucoside Synthesis by Glucoamylase or β-Glucosidase in organic Solvents," *Biotechnology Letters,* Vol. 14, No. 3, pp. 169–174 (March 1992).

Both the above-mentioned articles describe biocatalysed alkyl glycoside synthesis in the presence of a β-glucosidase and both teach that the synthesis is effected by the carbon chain length of the alcohol used, the first article stating that "for both enzymes an augmentation of carbon chain length involves a decrease of synthesis yields," and the second article even more unequivocally stating that:

"Experiments carried out under the same conditions with C12 lauric alcohol led to virtually nil yield, which confirms the previous hypothesis. Moreover, if the line in FIG. 2 is extrapolated, it can be seen that beyond a chain length of 9 to 10 carbons, the synthesis reaction should not be possible under our experimental conditions."

With the above state of the art in mind, it has now been surprisingly found that, contrary to the teachings in said articles, an enzyme-catalysed direct reaction between a glucose reactant and a long chain $C_8$ to $C_{18}$ fatty alcohol is indeed possible.

Thus, the present invention provides a process for the preparation of long-chain alkyl glycosides, comprising reacting a glucose-containing reactant and a $C_8$–$C_{18}$ fatty alcohol in the presence of a glucosidase and a reaction promoter effective to promote the formation of said alkyl glycoside when said promoter is present in an amount of less than about 50 wt % of the total reaction mixture.

Preferably, said glucose-containing reactant is obtained from starch hydrolysis, and said reaction is carried out in the presence of a β-glucosidase.

In especially preferred embodiments of the present invention, there is provided a process for the preparation of long-chain alkyl glycosides, comprising reacting a glucose-containing reactant obtained from starch hydrolysis and a $C_8$ to $C_{18}$ fatty alcohol in the presence of a β-glucosidase and a reaction promoter selected from the group consisting of a $C_1$–$C_4$ alcohol, SDS, a long-chain alkyl glucoside, dioxane, acetone, dimethylsulfoxide, and sulfobutanedioic acid 1,4-bis (2-ethylhexyl) ester sodium salt and mixtures thereof at a pH of about 3.5–7.0 and a temperature of up to about 70° C., wherein said reaction promoter constitutes less than 50% by weight of the reactive mixture.

The term "$C_8$ to $C_{18}$ fatty alcohols" as used herein is intended to denote the use of a single such alcohol, or a mixture of two or more such fatty alcohols.

In preferred embodiments of the present invention, said β-glucosidase is extracted from almonds, and said additive is methanol.

Preferably, said reaction is carried out for a period of at least ten hours.

In especially preferred embodiments of the invention, said reaction promoter constitutes less than 30% by weight of the reactive mixture, and said fatty alcohol is a $C_{10}$–$C_{18}$ fatty alcohol.

In other preferred embodiments of the present invention said reaction promoter is selected from the group consisting of formamide, methyl formamide and dimethyl formamide.

Hildebrand and Scott designated the energy of vaporization per $Cm^2$ as the cohesive energy density and its square root as the solubility parameter. It is assumed that the cohesive energy, $\Delta E$, arises from contributions from hydrogen bonding $\Delta E_H$, as well as permanent-dipole-permanent-dipole interactions, $\Delta E_P$ and nonpolar interaction, $\Delta E_D$. The square roots of $\Delta E_H$, $\Delta E_P$ and $\Delta E_D$ per $Cm^2$ are the hydrogen bonding, polar and dispersion components of the solubility parameter. It was found that the first two are sufficient for selecting a suitable promoter for the reaction. Solubility parameter components for various compounds could be found in many sources including Kirk Othmer's Encyclopedia of Chemical Technology.

It was found that the most suitable promoters for the reaction in the present invention have a polar component of solubility parameter in the range of 5–13 and a hydrogen bonding component of solubility parameter in the range of 4–11.

In another aspect of the present invention, there is provided a process for the preparation of long-chain alkyl glycosides, comprising reacting a glucose-containing reactant obtained from starch hydrolysis and a $C_8$ to $C_{18}$ fatty alcohol in the presence of an α-glucosidase, a β-glucosidase, glucoamylase, glucosyltransferase or a mixture thereof, and a reaction promoter selected from the group consisting of methanol, ethanol, and isopropanol and mixtures thereof, at a pH of about 3.5–7.0 and a temperature of up to about 70° C., wherein said reaction promoter constitutes less than 50% by weight of the reactive mixture; said process further comprising the steps of separating the resulting aqueous and organic phases, and removing said reaction promoter from said organic phase, whereupon said remaining organic phase separates into a first phase containing excess reagent and a second phase containing the long-chain alkyl glucoside product.

The enzymes used in the process of the present invention may be dissolved or immobilized, and thus said enzymes can be present in either of the above forms during the reaction.

It is known that alcohol solubility in water decreases with increasing alkyl chain length (propanol is fully miscible, butanol—7.8%, hexanol—0.58%, octanol—0.06% and decanol <0.01%). Low solubility might be one explanation for decrease in synthesis yield with augmentation of chain length. Increasing fatty alcohol concentration next to the enzyme can be achieved through application of a cosolvent, a compound that dissolves both the aqueous solution of the glucose containing the reagent and the fatty alcohol. G. Vic, et al. [*Tetrahedron Letters*, Vol. 33, pp. 4567–4570 (1992)] have tested the enzymatic reaction of glucose and alcohols with up to 8 carbon atoms. The co-solvent in the single phase system was acetonitrile and its content in the system was 9 times the content of all other components. Such high proportions of co-solvent increase the volume to be handled and thereby the capital cost. In addition, it dilutes the product and increases the operation costs for product separation and concentration.

Thus, it will be realized that there is no simple explanation, and it is also not readily evident, how the system of the present invention succeeds in the preparation of long-chain alkyl glucosides when the prior art failed to do so.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

As will be seen hereinafter, Example 1 shows that the addition of methanol in proportion of about 0.2 units per unit of total reaction mixture, far from being sufficient for combining the phase into one, provided for the reaction that was not possible without it [see Comparative Example A]. Some of the reaction promoters used for this invention may improve the solubility of the fatty alcohol. That is, however, not their major role. It was surprisingly found [see Comparative Example B] that methyl ethyl ketone (MEK, 2-butanone), which is known as a very efficient co-solvent, is not an efficient reaction promoter for the present invention, giving yields of less than 28%, less than 27%, and less than 6% compared to ethanol, dimethyl sulfoxide and methanol respectively, as seen from the results of Example 1 when compared with the results of Example B.

Surfactants may improve the contact between the phases and were suggested for chemically-catalyzed reactions. Surprisingly, it was found that efficient surfactants such as CTAB and Triton X-100 contribute to the enzymatic reaction much less than SDS [see Comparative Example C]. In a way, the fact that any surfactant enhances the reaction might be unexpected, as surfactants tend to denaturate the enzyme.

An even more surprising finding is the fact that $C_1$–$C_4$ alcohols are suitable reaction promoters. Their reaction with glucose is preferred over the reaction of the fatty alcohols with glucose, both thermodynamically and kinetically. Their introduction into the system would have been expected to decrease product yield through competition. Yet, comparing Example 1 and Comparative Example A, the opposite effect is self-evident.

Low solubility in the aqueous phase is probably not the sole explanation for lower yields at higher carbon chain lengths. Unlike solubility, other parameters may not show a gradal dependence on the number of carbon atoms. Thus, beyond a certain molecular weight, the fatty alcohol size is so large that it prevents the substrate access of the active site of the enzyme, avoiding the reaction completely. Similarly, beyond a certain alkyl chain length, the product may be very active in denaturating the enzyme. Therefore, enzymatic production of hexyl and octylglucoside does not teach that production of dodecylglucoside, for example, is feasible.

COMPARATIVE EXAMPLE A

In a screwed cap Appendorf vial of a total volume of 1.5 ml, 100 mg glucose, 500 mg dodecanol and 40 units of β-glucosidase (from almonds) dissolved in 100 μl buffer acetate solution (pH=4.75) were mixed together for 8 days at 30° C. No detectable amount of dodecyl glucoside was found by HPLC analysis of the organic phase.

EXAMPLE 1

In a screwed cap Appendorf vial of a total volume of 1.5 ml, 100 mg glucose, 450 mg dodecanol, 100 mg methanol and 40 units of β-glucosidase (from almonds) dissolved in 100 μl buffer acetate solution (pH=4.75) were mixed together for 3 days at 37° C. 1.84 mg dodecyl glucoside was found by HPLC analysis of the organic phase.

In a similar experiment, 200 mg of ethanol, DMSO or dioxane were tested as additives at the same conditions. The amounts of dodecyl glucoside found were 0.35, 0.37 and 0.20 mg, respectively.

COMPARATIVE EXAMPLE B

The experiment described in Example 1 was repeated, using 200 mg of 2-butanone as an additive. The amount of dodecyl glucoside produced was less than 0.1 mg.

EXAMPLE 2

The experiment described in Example 1 was repeated, using 8.5 mg of Aerosol OT-100 as an additive. 0.12 mg of dodecyl glucoside were found in the organic phase. More product was found in the aqueous phase.

COMPARATIVE EXAMPLE C

The experiment described in Example 1 was repeated, using 50 μL of 0.1 molar hexadecyltrimethylammonium bromide (CTAB) solution as an additive. The amount of product found was less than 0.05 mg.

EXAMPLE 3

Experiment 1 was repeated with an extension of the mixing time to 8 days, after which the organic phase was separated from the aqueous phase and heated for methanol distillation. On cooling, two phases were found: one containing mainly dodecanol, and another containing mainly the product dodecyl glucoside.

EXAMPLE 4

Many additional experiments were made testing the effects of various parameters such as:
a. The glucose source: Both glucose and β-methyl glucoside were tested as substrates to the enzymatic reaction. β-methyl glucoside can be formed by an enzymatic reaction between flucose and methanol using 3-glucosidase. These enzymatic reactions are known to be very efficient in both yield and rate.
b. Temperature: The range of temperatures tested was 35–70° C.
c. The chain length of the fatty alcohol: Most of the work focussed on dodecanol and on octanol.
d. Promoter: Many promoters were tested, including methanol, formamide, acetamide, ethyl acetate, glycerol, isopropanol and sodium dodecyl sulfonate (SDS). Combinations of promoters were tested also.
e. The buffer tested: Both acetate and phosphate buffers were tested.
f. The ratio between the various components in the system: Various ratios between the the buffer solution, the promoter and the fatty alcohols were tested. The content of the promoter ranged between 8% and 31% of the total raction mixture.

The experiments were conducted similarly to the procedure in Example 1. About 100 mg of glucose or methyl glucoside, an acetate or phosphate ester (0.1 M, pH=4.75 in most cases), β-methyl glucosidase (20–100 units, supported or dissolved in the buffer solution), the fatty alcohol (450–1400 mg) and the promoter were mixed strongly for 1–10 days in a screwed cap Appendorf vial held at the desired temperature. Then the fatty alcohol phase was analysed to determine the concentration of the long chain alkyl glycoside in it.

Representative results are shown in the table. The abbreviations used in this table are:
temp.—temperature, R—rate, G—glucose, MG—β methyl glycoside, Phos.—phosphate, Ac—acetate, DoOH—dodecanol, OctOH—octanol, FA—formamide, DMSO—dimethnyl sulfoxide, MeOH—methanol, IPA—isopropyl alcohol, EtAc—ethyl acetate, AcAm—acetamide.

The amounts are given in miligrams and the reaction rate is presented in terms of micromoles per day per 100 units of enzyme.

The results show that the rate of octyl glucoside and dodecyl glucoside formation are high using various promoters and reaction conditions. It is interesting to note that contrary to the expectation from the prior art, higher proportions of promoter are not always beneficial. In tests #7 and #9 the promoter content was 31% of the total reaction mixture and the results were significantly lower than in tests #4 and #8 (dodecanol) and #15 and #16 where the content of the promoter was about 18%.

|  | Glucose Source | Buffer Type | Buffer Amount | Temp. | Alkanol Type | Alkanol Amount | Promoter I Type | Promoter I Amount | Promoter II Type | Promoter II Amount | R |
|---|---|---|---|---|---|---|---|---|---|---|---|
| 1. | MG | Phos | 41 | 50 | DoOH | 700 | FA | 154 | | | 14.5 |
| 2. | MG | Phos | 100 | 50 | DoOH | 700 | DMSO | 200 | | | 13.5 |
| 3. | MG | Phos | 100 | 50 | DoOH | 700 | Gly | 200 | | | 10.2 |
| 4. | MG | Phos | 40 | 50 | DoOH | 700 | FA | 160 | | | 40.2 |
| 5. | MG | Phos | 59 | 50 | DoOH | 700 | FA | 160 | MeOH | 26 | 20.7 |
| 6. | MG | Phos | 48 | 50 | DoOH | 700 | FA | 160 | MeOH | 26 | 17.1 |
| 7. | G | Phos | 100 | 50 | DoOH | 700 | FA | 160 | MeOH | 200 | <1 |
| 8. | G | Phos | 61 | 50 | DoOH | 700 | FA | 160 | | | 43.4 |
| 9. | G | Phos | 104 | 50 | DoOH | 700 | FA | 160 | IPA | 200 | 2.6 |
| 10. | G | Phos | 60 | 45 | DoOH | 700 | MeOH | 100 | 01M SDS | 60 | 10.6 |
| 11. | MG | Phos | 75 | 50 | DoOH | 1400 | FA | 300 | | | 28.2 |
| 12. | MG | Phos | 41 | 45 | DoOH | 700 | FA | 140 | | | 18.8 |
| 13. | G | Phos | 100 | 45 | OctOH | 700 | MeOH | 200 | | | 95.2 |
| 14. | G | Phos | 100 | 45 | OctOH | 700 | MeOH | 150 | | | 119.6 |
| 15. | MG | Phos | 100 | 50 | OctOH | 700 | FA | 140 | | | 404 |
| 16. | MG | Phos | 50 | 50 | OctOH | 700 | FA | 140 | | | 529 |
| 17. | MG | Phos | 47 | 50 | DoOH | 700 | FA | 165 | | | 40.2 |
| 18. | G | Phos | 50 | 45 | DoOH | 450 | FA | 100 | | | 17.6 |
| 19. | G | Phos | 60 | 50 | DoOH | 700 | MeOH | 100 | | | 7.8 |
| 20. | MG | Phos | 20 | 45 | DoOH | 500 | FA | 100 | | | 27.9 |
| 21. | MG | Phos | 100 | 50 | DoOH | 700 | EtAc | 200 | | | 6.9 |
| 22. | MG | Phos | 51 | 50 | DoOH | 700 | AcAm | 67 | | | 9.8 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for preparation of long-chain alkyl glycosides in a multiphase system, comprising reacting a glucose-containing reactant with a $C_8$–$C_{18}$ fatty alcohol in the presence of a β-glucosidase and a reaction promoter, wherein said promoter is selected from the group consisting of formamide, methyl formamide, dimethyl formamide, a $C_1$–$C_4$ alcohol, dioxane, acetone, dimethylsulfoxide, mixtures thereof, and solvents having a polar component of solubility parameter in the range of 5–13, and a hydrogen bonding component of solubility parameter in the range of 4–11 and said promoter is present in an amount of less than 50 wt % of the total reaction mixture.

2. A process according to claim 1, wherein said glucose-containing reactant is obtained from starch hydrolysis.

3. A process according to claim 1, wherein said reaction promoter is selected from the group consisting of a $C_1$–$C_4$ alcohol, dioxane, acetone, dimethylsulfoxide, and mixtures thereof, and the reaction is effected at a pH of about 3.5–7.0 and a temperature of up to about 70° C.

4. A process according to claim 3, wherein said β-glucosidase is extracted from almonds.

5. A process according to claim 1, wherein said reaction is carried out for a period of at least ten hours.

6. A process according to claim 1, wherein said reaction promoter constitutes less than 30% by weight of the reactive mixture.

7. A process according to claim 1, wherein said reaction promoter is selected from the group consisting of formamide, methyl formamide and dimethyl formamide.

8. A process according to claim 1, wherein said reaction promoter is selected from the group consisting of solvents having a polar component of solubility parameter in the range 5–13, and a hydrogen bonding component of solubility parameter in the range of 4–11.

9. A process according to claim 1, wherein said fatty alcohol is a $C_{10}$–$C_{18}$ fatty alcohol.

10. A process according to claim 1, wherein said reaction promoter comprises methanol.

11. A process for preparation of long-chain alkyl glycosides in a multiphase system, comprising:

reacting a glucose-containing reactant obtained from starch hydrolysis and a $C_8$ to $C_{18}$ fatty alcohol in the presence of a β-glucosidase, optionally together with one or more enzymes selected from an α-glucosidase, glucoamylase, and glucosyltransferase, and a reaction promoter selected from the group consisting of methanol, ethanol, isopropanol and mixtures thereof, at a pH of about 3.5–7.0 and a temperature of up to about 70° C., wherein said reaction promoter constitutes less than 50% by weight of the reactive mixture;

said process further comprising the steps of separating the resulting aqueous and organic phases, and removing said reaction promoter from said organic phase, whereupon the remaining organic phase separates into a first phase containing excess reagent and a second phase containing the long-chain alkyl glucoside product.

* * * * *

UNITED STATES PATENT AND TRADEMARK OFFICE
CERTIFICATE OF CORRECTION

| | |
|---|---|
| PATENT NO. | : 6,037,151 |
| DATED | : March 14, 2000 |
| INVENTOR(S) | : Aharon Meir Eyal. |

It is certified that error appears in the above-identified patent and that said Letters Patent is hereby corrected as shown below:

<u>Title page,</u>
U.S. Application Data,
After Item [63] Continuation of Application No. delete "08/809,330" and insert -- 08/809,730" -- delete Patent No. "5,845,507".

Signed and Sealed this

Fourth Day of December, 2001

*Attest:*

NICHOLAS P. GODICI
*Attesting Officer — Acting Director of the United States Patent and Trademark Office*